United States Patent
Patil et al.

(10) Patent No.: US 9,663,518 B1
(45) Date of Patent: May 30, 2017

(54) PROCESS FOR PREPARATION OF (2S, 5R)-1,6-DIAZA-BICYCLO[3.2.1]OCTANE-2-CARBONITRILE-7-OXO-6-(SULFOOXY)-MONO SODIUM SALT

(71) Applicant: WOCKHARDT LIMITED, Aurangabad (IN)

(72) Inventors: Vijaykumar Jagdishwar Patil, Solapur (IN); Ravikumar Tadiparthi, Aurangabad (IN); Satish Birajdar, Latur (IN); Bharat Dond, Aurangabad (IN); Mahesh Vithalbhai Patel, Aurangabad (IN)

(73) Assignee: WOCKHARDT LIMITED, Chikalthana, Aurangabad (IN)

( * ) Notice: Subject to any disclaimer, the term of this patent is extended or adjusted under 35 U.S.C. 154(b) by 0 days.

(21) Appl. No.: 15/115,668

(22) PCT Filed: Feb. 2, 2015

(86) PCT No.: PCT/IB2015/050771
§ 371 (c)(1),
(2) Date: Jul. 30, 2016

(87) PCT Pub. No.: WO2015/114595
PCT Pub. Date: Aug. 6, 2015

(30) Foreign Application Priority Data

Feb. 3, 2014 (IN) .............. 382/MUM/2014

(51) Int. Cl.
*C07D 401/04* (2006.01)
*C07D 471/08* (2006.01)

(52) U.S. Cl.
CPC .................. *C07D 471/08* (2013.01)

(58) Field of Classification Search
CPC ........................................ C07D 401/04
USPC .......................................... 546/121
See application file for complete search history.

(56) References Cited

FOREIGN PATENT DOCUMENTS

| | | |
|---|---|---|
| EP | 2657234 A1 | 10/2013 |
| WO | WO2013038330 A1 | 3/2013 |
| WO | WO2014135930 A | 9/2014 |

*Primary Examiner* — Niloofar Rahmani
(74) *Attorney, Agent, or Firm* — Bio Intellectual Property Services LLC; O. (Sam) Zaghmout

(57) ABSTRACT

A process for preparation of a compound of Formula (I) is disclosed.

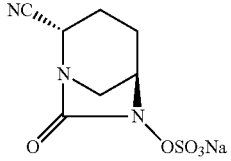

Formula (I)

14 Claims, No Drawings

PROCESS FOR PREPARATION OF (2S, 5R)-1,6-DIAZA-BICYCLO[3.2.1]OCTANE-2-CARBONITRILE-7-OXO-6-(SULFOOXY)-MONO SODIUM SALT

RELATED PATENT APPLICATIONS

This patent application claims priority to Indian Patent Application No. 382/MUM/2014 filed on Feb. 3, 2014, the disclosures of which are incorporated herein by reference in its entirety as if fully rewritten herein.

FIELD OF THE INVENTION

The invention relates to a process for preparation of (2S,5R)-1,6-diaza-bicyclo[3.2.1]octane-2-carbonitrile-7-oxo-6-(sulfooxy)-mono sodium salt.

BACKGROUND OF THE INVENTION

A compound of Formula (I), chemically known as (2S, 5R)-1,6-diaza-bicyclo[3.2.1]octane-2-carbonitrile-7-oxo-6-(sulfooxy)-mono sodium salt has antibacterial properties and is disclosed in PCT International Patent Application No. PCT/IB2012/054706. The present invention discloses a process for preparation of a compound of Formula (I).

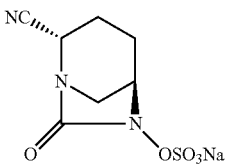

Formula (I)

SUMMARY OF THE INVENTION

In one general aspect, there is provided a process for preparation of a compound of Formula (I), comprising:

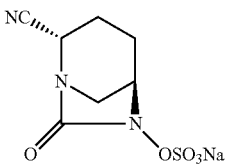

Formula (I)

(a) converting a compound of Formula (II) to a compound of Formula (III);

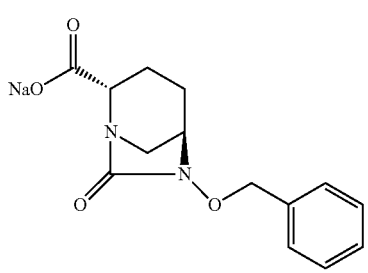

Formula (II)

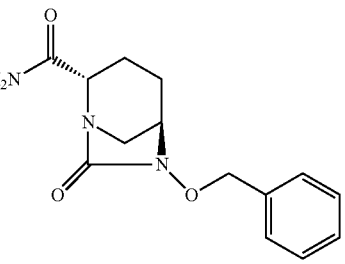

Formula (III)

(b) reacting a compound of Formula (III) with a dehydrating agent to obtain a compound of Formula (IV);

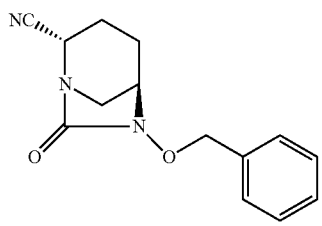

Formula (IV)

(c) hydrogenolysis of a compound of Formula (IV) to obtain a compound of Formula (V);

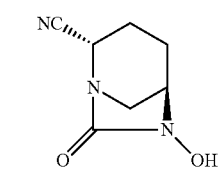

Formula (V)

(d) converting a compound of Formula (V) to a compound of Formula (VI); and

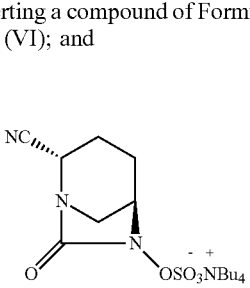

Formula (VI)

(e) converting a compound of Formula (VI) to a compound of Formula (I).

The details of one or more embodiments of the inventions are set forth in the description below. Other features, objects and advantages of the inventions will be apparent from the following description including claims.

DETAILED DESCRIPTION OF THE INVENTION

Reference will now be made to the exemplary embodiments, and specific language will be used herein to describe the same. It should nevertheless be understood that no limitation of the scope of the invention is thereby intended. Alterations and further modifications of the inventive features illustrated herein, which would occur to one skilled in the relevant art and having possession of this disclosure, are to be considered within the scope of the invention. It must be noted that, as used in this specification and the appended claims, the singular forms "a", "an", and "the" include plural referents unless the content clearly dictates otherwise. All references including patents, patent applications, and literature cited in the specification are expressly incorporated herein by reference in their entirety.

In one general aspect, there is provided a process for preparation of a compound of Formula (I), comprising:

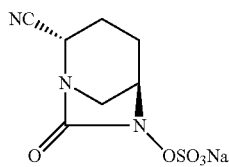

Formula (I)

(a) converting a compound of Formula (II) to a compound of Formula (III);

Formula (II)

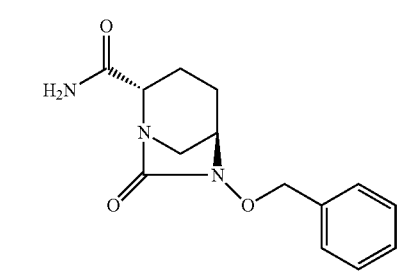

Formula (III)

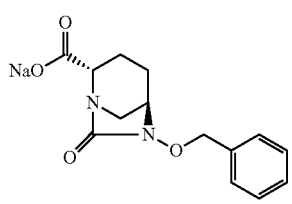

(b) reacting a compound of Formula (III) with a dehydrating agent to obtain a compound of Formula (IV);

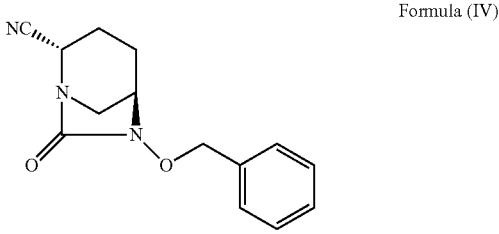

Formula (IV)

(c) hydrogenolysis of a compound of Formula (IV) to obtain a compound of Formula (V);

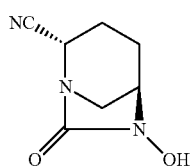

Formula (V)

(d) converting a compound of Formula (V) to a compound of Formula (VI); and

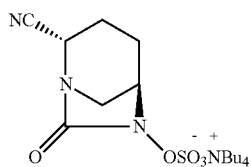

Formula (VI)

(e) converting a compound of Formula (VI) to a compound of Formula (I).

Scheme 1

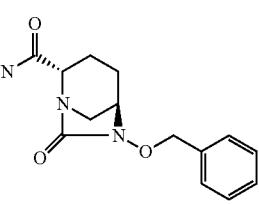

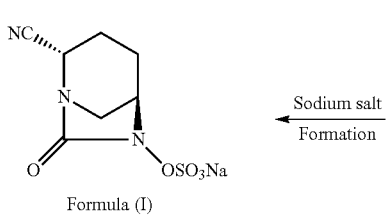 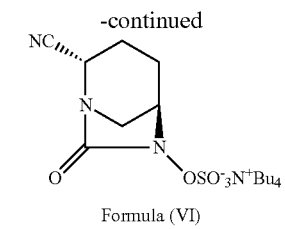 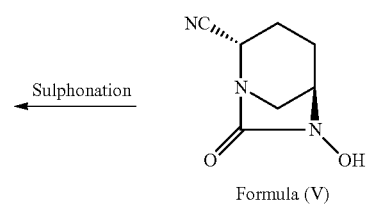

Formula (I) ← Sodium salt Formation — Formula (VI) ← Sulphonation — Formula (V)

In some embodiments, a compound of Formula (I) is prepared by using a general procedure described in Scheme 1. Typically, a compound of Formula (I) is prepared from a compound of Formula (II). A compound of Formula (II) is reacted with a suitable acylating agent in presence of suitable solvent and suitable base, followed by the reaction with aqueous ammonia, to obtain a compound of Formula (III). Typical, non-limiting examples of acylating agent include pivaloyl chloride, ethylchloroformate and the like. Typical, non-limiting examples of solvent include dichloromethane, dimethylformamide, tetrahydrofuran, dimethylacetamide, dioxane or a mixture thereof. Typical, non-limiting examples of bases include triethylamine, triethylamine hydrochloride, 1-methyl-2-pyrrolidinone, 1-methylpyrrolidine, N-methylmorpholine, N-ethyldiisopropylamine or a mixture thereof. In some embodiments, a compound of Formula (II) is reacted with pivaloyl chloride in presence of tetrahydrofuran as solvent and 1-methyl-2-pyrrolidine as base, followed by the reaction with aqueous ammonia, to obtain a compound of Formula (III). The compound of Formula (III) is recrystallized form suitable solvent such as n-butyl chloride. In some embodiments, compound of Formula (III) is having a purity of more than about 98% as determined by HPLC.

The compound of Formula (III) is dehydrated with a suitable reagent to obtain a compound of Formula (IV). Typical, non-limiting examples of dehydrating agent include trifluoroacetic anhydride, thionyl chloride, phosphorous oxychloride, acetic anhydride, phosphorous pentoxide, N,N'-carbonyldiimidazole, dicyclohexylcabodimide, diphenylhydrogen phosphonate, bis(triphenyl)oxodiphosphoniumtrifluoromethane sulfonate, 1-trifluoroacetyl imidazole, 2,4,6-trichlorotriazine, 1,1'-carbonyldibenzotriazole, 1,1'-sulfonyldibenzotriazole, diethylchlorophosphate, hexamethylphosphorous triamide, titanium tetrachloride or a mixture thereof. In some embodiments, a compound of Formula (III) is dehydrated in presence of trifluoroacetic anhydride to obtain a compound of Formula (IV).

The compound of Formula (V) is obtained by hydrogenolysis of a compound of Formula (IV). In some embodiments, hydrogenolysis of a compound of Formula (IV) to obtain a compound of Formula (V) is carried out in presence of a transition metal catalyst and a hydrogen source. Typical, non-limiting examples of transition metal include platinum, palladium, rhodium, ruthenium, nickel and the like. Typical, non-limiting examples of hydrogen source include hydrogen gas, ammonium formate, cyclohexene and the like. In some other embodiments, the transition metal catalyst is palladium on carbon and hydrogen source is hydrogen gas. In some other embodiments, the hydrogenolysis reaction is carried out in presence of a suitable solvent such as dichloromethane, dimethylformamide, alcohol, acetone, tetrahydrofuran, ethyl acetate, dioxane or a mixture thereof. In some embodiments, the hydrogenolysis of a compound of Formula (IV) to obtain a compound of Formula (V) is carried out using 10% palladium on carbon catalyst, and in presence of a mixture of dichloromethane and dimethylformamide as solvent.

The compound of Formula (V) is reacted with a suitable sulfonating reagent in presence of suitable solvent, followed by treatment with tetrabutylammonium acetate to obtain a compound of Formula (VI). Typical non-limiting examples of sulphonating reagent include sulfur trioxide pyridine complex, sulfur trioxide dimethylformamide complex or sulfur trioxide triethylamine complex and the like. In some embodiments, compound of Formula (V) is reacted with sulfur trioxide dimethylformamide complex in presence of suitable solvent such as dimethylformamide to obtain the sulfonated compound. In some embodiments, the sulfonated compound is further treated with terabutylammonium acetate in presence of suitable solvent such as water to obtain a compound of Formula (VI).

The sodium salt formation of compound of Formula (VI) is done by treating with suitable reagent to obtain a compound of Formula (I). Typical, non-limiting methods for sodium salt formation include treating with amberlite sodium, sodium ethyl hexanoate or inorganic bases such as sodium carbonate or sodium bicarbonate. In some embodiments, compound of Formula (VI) is converted to a compound of Formula (I) by treating with amberlite sodium. In some embodiments, compound of Formula (VI) is dissolved in suitable solvent such as 10% tetrahydrofuran in water and is passed through the column packed with Amberlite 200 sodium resin to provide a compound of Formula (I). In some embodiments, compound of Formula (I) has a purity of more than about of 98% as determined by HPLC.

In some embodiments, there is provided a process for preparation of a compound of Formula (I) having a purity of more than about 98% as determined by HPLC.

In some embodiments, there is provided a pharmaceutical composition comprising a compound of Formula (I) having a purity of more than about 98% as determined by HPLC. In some other embodiments, pharmaceutical composition may further comprise one or more pharmaceutically acceptable excipients.

In some embodiments, compound of Formula (I) is prepared using a process described in Scheme I.

In some embodiments, there is provided a process for preparation of a compound of Formula (I), comprising:

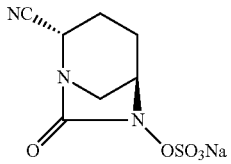

Formula (I)

(a) reacting a compound of Formula (II) with pivaloyl chloride in presence of N-methylmorpholine and tetrahydrofuran, followed by reaction with aqueous ammonia to obtain a compound of Formula (III);

Formula (II)

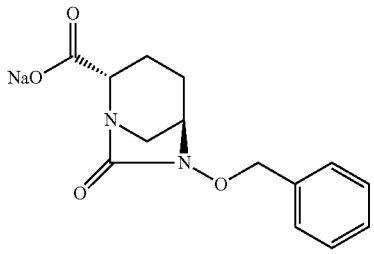

Formula (III)

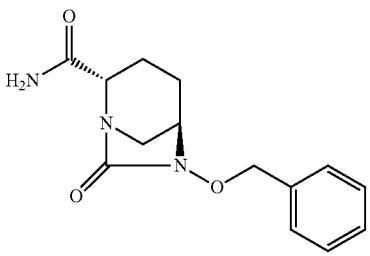

(b) reacting a compound of Formula (III) with trifluoroacetic anhydride in presence of triethylamine and dichloromethane to obtain a compound of Formula (IV);

Formula (IV)

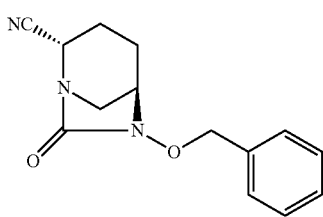

(c) hydrogenolysis of a compound of Formula (IV) over palladium on carbon to obtain a compound of Formula (V);

Formula (V)

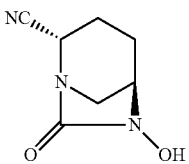

(d) reacting a compound of Formula (V) with sulfur trioxide-dimethylformamide complex, followed by treatment with tetrabutylammonium acetate to obtain a compound of Formula (VI); and Formula (VI)

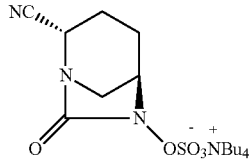

(e) contacting a compound of Formula (VI) with Amberlite 200 sodium resin to obtain a compound of Formula (I).

It will be readily apparent to one skilled in the art that varying substitutions and modifications may be made to the invention disclosed herein without departing from the scope and spirit of the invention. For example, those skilled in the art will recognize that the invention may be practiced using a variety of different compounds within the described generic descriptions.

EXAMPLES

The following examples illustrate the embodiments of the invention that are presently best known. However, it is to be understood that the following are only exemplary or illustrative of the application of the principles of the present invention. Numerous modifications and alternative compositions, methods, and systems may be devised by those skilled in the art without departing from the spirit and scope of the present invention. The appended claims are intended to cover such modifications and arrangements. Thus, while the present invention has been described above with particularity, the following examples provide further detail in connection with what are presently deemed to be the most practical and preferred embodiments of the invention.

Example 1

Synthesis of (2S,5R)-1,6-diaza-bicyclo[3.2.1]octane-2-carbonitrile-7-oxo-6-(sulfooxy)-mono sodium Salt Step 1: Synthesis of (2S,5R)-6-(benzyloxy)-7-oxo-1,6-diaza-bicyclo[3.2.1]octane-2-carboxamide (III)

Method 1:

To a stirred suspension of sodium (2S,5R)-6-(benzyloxy)-7-oxo-1,6-diazabicyclo[3.2.1]octane-2-carboxylate (II) (1 g, 0.00335 mol) in dichloromethane (15 ml), triethylamine hydrochloride (0.688 g, 0.00503 mol) was added in small portions at 25° C. After 30 minutes, triethylamine (0.678 g, 0.0067 moles) was added, followed by addition of pivaloyl chloride (0.605 g, 0.00502 mol) at 0-5° C. under stirring. After 2 hours, the reaction mass was cooled further to −20° C. and aqueous ammonia (25% solution, 0.75 ml, 0.01 mol) was added slowly. The completion of the reaction was confirmed after 30 minutes by thin layer chromatography using acetone:hexane (35:65) solvents. The reaction mixture was diluted with water (10 ml) and the mixture was allowed to warm to room temperature. The dichloromethane layer was separated and the aqueous layer was re-extracted with dichloromethane (5 ml). The combined organic layer was dried (over anhydrous sodium sulfate) and the solvent was evaporated under reduced pressure. The residue was purified by re-crystallization from n-butyl chloride to obtain 0.75 g of (2S,5R)-6-(benzyloxy)-7-oxo-1,6-diaza-bicyclo[3.2.1]octane-2-carboxamide (III) as an off-white solid in 81% yield.

Analysis:

Mass: 276.1 (M+1) for Molecular Weight of 275.31 and Molecular Formula of $C_{14}H_{17}N_3O_3$;

$^1$H NMR (400 MHz, CDCl$_3$): δ 7.43-7.35 (m, 5H), 6.56 (brs, 1H), 5.58 (brs, 1H), 5.07-4.89 (dd, 2H), 3.95-0.393 (d, 1H), 3.31 (s, 1H), 3.04-3.01 (d, 1H), 2.78-2.75 (d, 1H), 2.38-2.32 (m, 1H), 2.03-1.88 (m, 2H), 1.64-1.58 (m, 1H);

Purity as determined by HPLC: 98.9%.

Method 2:

To a stirred suspension of sodium (2S,5R)-6-(benzyloxy)-7-oxo-1,6-diazabicyclo[3.2.1]octane-2-carboxylate (II) (5 g, 0.0167 mol) in dimethylformamide (25 ml) pivaloyl chloride (3.03 g, 0.0251 mol) was added drop wise at about 0-5° C. After stirring for 3 hours, the resulting mixture was cooled to −20° C. and aqueous ammonia (25% solution, 3.75 ml, 0.0501 mol) was added slowly under stirring. The completion of the reaction was confirmed after 30 minutes by thin layer chromatography using acetone:hexane (35:65) solvents. The reaction mixture was diluted with water (125 ml) and dichloromethane (50 ml), and allowed to warm to room temperature. The dichloromethane layer was separated and the aqueous layer extracted with fresh dichloromethane (25 ml). The combined organic layer was dried (over anhydrous sodium sulfate) and the solvent was evaporated under reduced pressure. The residue was purified by re-crystallization using n-butyl chloride to obtain 0.7 g of (2S,5R)-6-(benzyloxy)-7-oxo-1,6-diaza-bicyclo[3.2.1]octane-2-carboxamide (III) as an off-white solid in 15% yield.

Analysis:

Purity as determined by HPLC: 93.9%.

Method 3:

To a stirred suspension of sodium (2S,5R)-6-(benzyloxy)-7-oxo-1,6-diazabicyclo[3.2.1]octane-2-carboxylate (II) (5 g, 0.0167 mol) in tetrahydrofuran (50 ml), 1-methyl-2-pyrrolidinone (7.44 g, 0.0751 mol) and pivaloyl chloride (8.0 g, 0.0668 mol) was added at about 0-5° C. After stirring for 3 hours the resulting mixture was cooled to −20° C. and aqueous ammonia (25% solution, 6.2 ml, 0.0835 mol) was added slowly under stirring. The completion of the reaction was confirmed after 30 minutes by thin layer chromatography using acetone:hexane (35:65) solvents. The reaction mixture was diluted with water (50 ml) and allowed to warm to room temperature. The tetrahydrofuran layer was separated and the aqueous layer was extracted with dichloromethane (25 ml). The combined organic layer was dried (over anhydrous sodium sulfate) and the solvent evaporated under reduced pressure. The residue was purified by re-crystallization from n-butyl chloride to obtain 2.32 g of (2S,5R)-6-(benzyloxy)-7-oxo-1,6-diaza-bicyclo[3.2.1]octane-2-carboxamide (III) in 50% yield.

Analysis:

Purity as determined by HPLC: 91.6%.

Method 4:

To a stirred suspension of sodium (2S,5R)-6-(benzyloxy)-7-oxo-1,6-diazabicyclo[3.2.1]octane-2-carboxylate (II) (5 g, 0.0167 mol) in tetrahydrofuran (50 ml), 1-methyl-2-pyrrolidine (6.39 g, 0.0751 mol) and pivaloyl chloride (8.0 g, 0.0668 mol) was added at about 0-5° C. After stirring for 3 hours, the resulting mixture was cooled to −20° C. and aqueous ammonia (25% solution, 6.2 ml, 0.0835 mol) was added slowly under stirring. The completion of the reaction was confirmed after 30 minutes by thin layer chromatography using acetone:hexane (35:65) solvents. The reaction mixture was diluted with water (50 ml) and allowed to warm to room temperature. The tetrahydrofuran layer was separated and the aqueous layer was extracted with dichloromethane (25 ml). The combined organic layer was dried (over anhydrous sodium sulfate) and the solvent was evaporated under reduced pressure. The residue was purified by re-crystallization from n-butyl chloride, to obtain 4.35 g of (2S,5R)-6-(benzyloxy)-7-oxo-1,6-diaza-bicyclo[3.2.1]octane-2-carboxamide (III) in 94% yield.

Analysis:

Purity as determined by HPLC: 97.6%.

Analytical data for (2S,5R)-6-(benzyloxy)-7-oxo-1,6-diaza-bicyclo[3.2.1]octane-2-carboxamide obtained from Method 2, 3 and 4 was consistent with that obtained in Method 1.

Step 2: Synthesis of (2S,5R)-6-(benzyloxy)-7-oxo-1,6-diaza-bicyclo[3.2.1]octane-2-carbonitrile (IV)

Trifluoroacetic anhydride (48 ml, 0.340 mol) was added slowly to a solution of (2S,5R)-6-(benzyloxy)-7-oxo-1,6-diaza-bicyclo[3.2.1]octane-2-carboxamide (III) (47 g, 0.170 mol) in dichloromethane, (1430 ml) containing triethylamine (107 ml, 0.765 mol), under stirring at about −5° C. After 2 hours, the reaction mixture was diluted with water (1450 ml) and the resulting mixture was stirred for further 15 minutes. The dichloromethane layer was separated, washed with aqueous saturated sodium bicarbonate solution (470 ml), brine (470 ml), dried (over anhydrous sodium sulfate) and concentrated under reduced pressure. The residue was purified by column chromatography over silica gel (60-120 mesh) using acetone: hexane (0-15% acetone in hexane) solvents. The combined solvent fractions were concentrated under reduced pressure to obtain 32 g of (2S,5R)-6-(benzyloxy)-7-oxo-1,6-diaza-bicyclo[3.2.1]octane-2-carbonitrile (IV) as a white solid in 74% yield.

Analysis:

Mass: 258 (M+1) for Molecular Weight of 257 and Molecular Formula of $C_{14}H_{15}N_3O_2$;

$^1$H NMR (400 MHz, DMSO): δ 7.42-7.36 (m, 5H), 5.06-4.88 (dd, 2H), 4.37-4.35 (d, 1H), 3.36-3.35 (m, 1H), 3.29-3.26 (d, 1H), 3.16-3.12 (m, 1H), 2.30-2.25 (m, 1H), 2.13-2.09 (m, 1H), 1.90-1.83 (m, 2H);

Purity as determined by HPLC: 100%.

Step 3: Synthesis of (2S,5R)-6-hydroxy-7-oxo-1,6-diaza-bicyclo[3.2.1]octane-2-carbonitrile (V)

A solution of (2S,5R)-6-(benzyloxy)-7-oxo-1,6-diaza-bicyclo[3.2.1]octane-2-carbonitrile (IV) (32 g, 0.124 mol) in a mixture of dimethylformamide and dichloromethane (1:1, 160 ml: 160 ml) containing 10% palladium on carbon (4.6 g, 50% wet) was hydrogenated at 50-55 psi for 2 hours at 25° C. The resulting mixture was filtered through a celite pad and residue was washed with mixture of dimethylformamide and dichloromethane (1:1, 25 ml: 25 ml). The solvent from the combined filtrates was evaporated under reduced pressure to obtain 20.66 g of (2S,5R)-6-hydroxy-7-oxo-1,6-diaza-bicyclo[3.2.1]octane-2-carbonitrile (V) as an oil. The obtained product was used as such for the next reaction without further purification.

Step 4: Synthesis of (2S,5R)-6-(sulfooxy)-7-oxo-1,6-diaza-bicyclo[3.2.1]octane-2-carbonitrile, tetrabutylammonium Salt (VI)

To a solution of (2S,5R)-6-hydroxy-7-oxo-1,6-diaza-bicyclo[3.2.1]octane-2-carbonitrile (20.66 g, 0.124 mol) in dimethylformamide (160 ml), sulfur trioxide dimethylformamide complex (22.8 g, 0.149 mol) was added in one portion under stirring at about −5° C. After 60 minutes of stirring, the completion of the reaction was monitored by thin layer chromatography using mixture of chloroform and methanol (9:1). To the resulting mixture was slowly added a solution of tetrabutylammonium acetate (48.6 g, 0.161 mol) in water (160 ml). After 1 hour of stirring, the solvent was evaporated under reduced pressure to obtain an oily residue. The oily residue was co-evaporated with xylene (2×200 ml), to yield a thick mass. This mass was partitioned between dichloromethane (320 ml) and water (320 ml). The organic layer was separated and the aqueous layer re-extracted with dichloromethane (160 ml). The combined organic extracts were washed with water (3×160 ml), dried (over anhydrous sodium sulfate) and the solvent was evaporated under reduced pressure at about 35° C. The residual oily mass was triturated with ether (3×160 ml), each time the ether layer was decanted and finally the residue was dried under reduced pressure, to obtain 52.5 g of (2S,5R)-6-(sulfooxy)-7-oxo-1,6-diaza-bicyclo[3.2.1]octane-2-carbonitrile, tetrabutyl ammonium salt (VI) as an oil in 86% yield.

Analysis:

Mass: 246 (M−1) as free sulfonic acid; for Molecular Weight of 488 and Molecular Formula of $C_{23}H_{44}N_4O_5S$;

$^1$H NMR (400 MHz, CDCl$_3$): δ 4.39 (brs, 1H), 4.34-4.32 (d, 1H), 3.41-3.33 (m, 2H), 3.27-3.22 (m, 8H), 2.28 (m, 2H), 1.89-1.84 (m, 2H), 1.67-1.59 (m, 8H), 1.47-1.37 (m, 8H), 1.00-0.96 (m, 12H);

Purity as determined by HPLC: 95.24%.

Step 5: Synthesis of (2S,5R)-1,6-diaza-bicyclo [3.2.1]octane-2-carbonitrile-7-oxo-6-(sulfooxy)-mono sodium Salt (I)

A column loaded with activated Amberlite 200 sodium resin (1200 gm) was washed with water followed by 10% tetrahydrofuran in water. A solution of (2S,5R)-6-(sulfooxy)-7-oxo-1,6-diaza-bicyclo[3.2.1]octane-2-carbonitrile, tetrabutylammonium salt (VI) (51.5 g, 0.105 mol) in tetrahydrofuran (50 ml) was poured over the column. The column was further eluted by using 10% tetrahydrofuran in water. Tetrahydrofuran from the combined fractions was evaporated under reduced pressure and the aqueous layer extracted with ethyl acetate (5×250 ml). The aqueous layer was stirred with neutral charcoal (3 g) for 1 hour and then filtered through celite bed and further washed with water (100 ml). The combined filtrate was evaporated under reduced pressure till free of moisture, to obtain 20.5 g of (2S,5R)-1,6-diaza-bicyclo[3.2.1]octane-2-carbonitrile-7-oxo-6-(sulfooxy)-mono sodium salt in 72% yield.

Analysis:

Mass: 246 (M−1) as free sulfonic acid; for Molecular Weight of 269 and Molecular Formula of $C_7H_8N_3O_5SNa$;

$^1$H NMR (400 MHz, DMSO): δ 4.56-4.54 (d, 1H), 4.08 (brs, 1H), 3.24-3.18 (m, 2H), 1.97-1.82 (m, 4H); and Purity as determined by HPLC: 98.46%.

The invention claimed is:

1. A process for preparation of a compound of Formula (I)

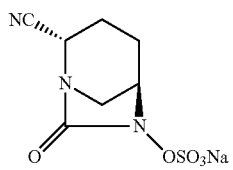

Formula (I)

wherein said process comprising:

(a) converting a compound of Formula (II) to a compound of Formula (III);

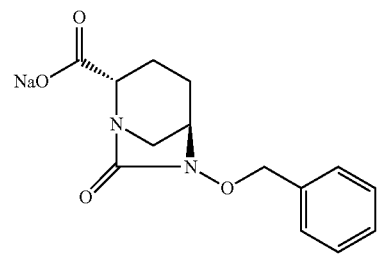

Formula (II)

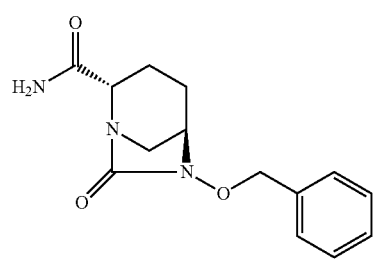

Formula (III)

(b) reacting the compound of Formula (III) with a dehydrating agent to obtain a compound of Formula (IV);

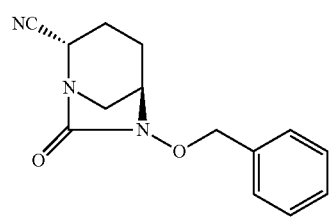

Formula (IV)

(c) hydrogenolysis of a compound of Formula (IV) to obtain a compound of Formula (V);

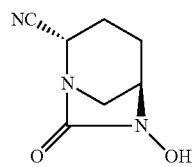

Formula (V)

(d) converting the compound of Formula (V) to a compound of Formula (VI); and

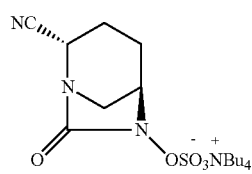

Formula (VI)

(e) converting the compound of Formula (VI) to the compound of Formula (I).

2. A process according to claim 1, wherein the compound of Formula (III) is obtained by reacting the compound of Formula (II) with an acylating agent in presence of a base and a solvent, followed by a reaction with an aqueous ammonia.

3. A process according to claim 2, wherein the acylating agent is selected from pivaloyl chloride or ethylchloroformate.

4. A process according to claim 2, wherein the base is selected from triethylamine, 1-methyl-2-pyrrolidinone, 1-methylpyrrolidine, N-methylmorpholine, N-ethyldiisopropylamine, or a mixture thereof.

5. A process according to claim 2, wherein the solvent is selected from dichloromethane, dimethylformamide, tetrahydrofuran, dimethylformamide, dioxane, or a mixture thereof.

6. A process according to claim 1, wherein the dehydrating agent in step (b) is selected from trifluoroacetic anhydride, thionyl chloride, phosphorous oxychloride, acetic anhydride, phosphorous pentoxide, N,N'-carbonyldiimidazole, dicyclohexylcabodimide, diphenylhydrogen phosphonate, bis(triphenyl)oxodiphosphoniumtrifluoromethane sulfonate, 1-trifluoroacetyl imidazole, 2,4,6-trichlorotriazine, 1,1'-carbonyldibenzotriazole, 1,1'-sulfonyldibenzotriazole, diethylchlorophosphate, hexamethylphosphorous triamide, titanium tetrachloride, or a mixture thereof.

7. A process according to claim 1, wherein the hydrogenolysis of the compound of Formula (IV) is carried out in presence of a transition metal catalyst, a hydrogen source and a solvent to obtain the compound of Formula (V).

8. A process according to claim 7, wherein the transition metal catalyst is palladium on carbon and the hydrogen source is hydrogen gas.

9. A process according to claim 7, wherein the solvent is selected from alcohol, dichloromethane, dimethylformamide, tetrahydrofuran, acetone, ethyl acetate, dioxane, or a mixture thereof.

10. A process according to claim 1, wherein the compound of Formula (VI) is obtained by reacting the compound of Formula (V) with a sulfonating agent, followed by treatment with tetrabutylammonium acetate.

11. A process according to claim 10, wherein the sulfonating agent is sulfur trioxide pyridine complex, sulfur trioxide dimethylformamide complex or sulfur trioxide triethylamine complex.

12. A process according to claim 1, wherein the compound of Formula (I) is obtained by contacting the compound of Formula (VI) with a sodium exchange resin.

13. A process according to claim 12, wherein sodium exchange resin is Amberlite 200.

14. A process for preparation of a compound of Formula (I)

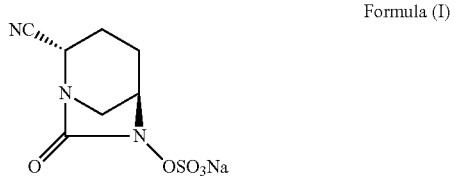

Formula (I)

wherein said process comprising:

(a) reacting a compound of Formula (II) with pivaloyl chloride in presence of N-methylmorpholine and tetrahydrofuran, followed by a reaction with aqueous ammonia to obtain a compound of Formula (III);

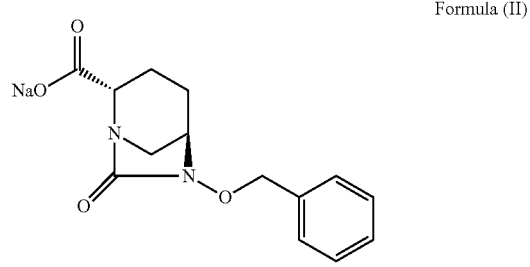

Formula (II)

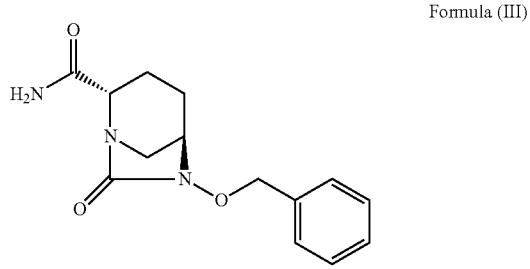

Formula (III)

(b) reacting the compound of Formula (III) with trifluoroacetic anhydride in presence of triethylamine and dichloromethane to obtain a compound of Formula (IV);

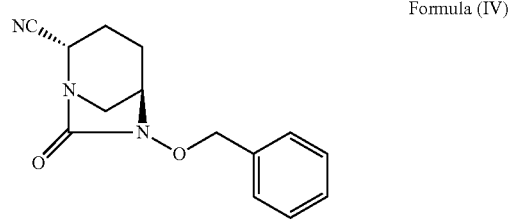 [SMILES: N#C[C@@H]1CC[C@@H]2CN1C(=O)N2OCc1ccccc1]

Formula (IV)

(c) hydrogenolysis of the compound of Formula (IV) over palladium on carbon to obtain a compound of Formula (V);

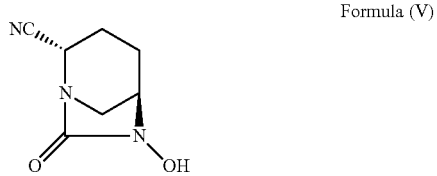 [SMILES: N#C[C@@H]1CC[C@@H]2CN1C(=O)N2O]

Formula (V)

(d) reacting the compound of Formula (V) with sulfur trioxide-dimethylformamide complex, followed by a treatment with tetrabutylammonium acetate to obtain a compound of Formula (VI)

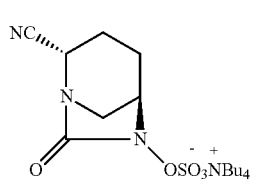
Formula (VI)
and
(e) contacting the compound of Formula (VI) with Amberlite 200 sodium resin to obtain the compound of Formula (I).
\* \* \* \* \*